United States Patent
Park et al.

(10) Patent No.: US 9,310,341 B2
(45) Date of Patent: Apr. 12, 2016

(54) METHOD AND SYSTEM FOR THREE-DIMENSIONAL VIBRATION MEASUREMENT USING VIBROMETER

(71) Applicant: GWANGJU INSTITUTE OF SCIENCE AND TECHNOLOGY, Buk-gu, Gwangju (KR)

(72) Inventors: Kyi Hwan Park, Gwangju (KR); Dong Kyu Kim, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 482 days.

(21) Appl. No.: 13/900,216

(22) Filed: May 22, 2013

(65) Prior Publication Data

US 2013/0312529 A1    Nov. 28, 2013

(30) Foreign Application Priority Data

May 22, 2012   (KR) .................. 10-2012-0054093

(51) Int. Cl.
*G01N 29/24* (2006.01)
*G01H 9/00* (2006.01)

(52) U.S. Cl.
CPC ............. *G01N 29/2418* (2013.01); *G01H 9/00* (2013.01)

(58) Field of Classification Search
CPC ................................. G01N 29/2418
USPC ........................................... 702/54
See application file for complete search history.

(56) References Cited

U.S. PATENT DOCUMENTS

| 6,256,359 B1 * | 7/2001 | Masumoto ............. H04H 60/44 329/304 |
| 2004/0125378 A1 * | 7/2004 | Selbach ................ G01M 15/12 356/496 |

FOREIGN PATENT DOCUMENTS

| JP | H07-248213 A | 9/1995 |
| JP | 3824597 B2 | 9/2006 |
| JP | 2008-286797 A | 11/2008 |

* cited by examiner

*Primary Examiner* — Bryan Bui
(74) *Attorney, Agent, or Firm* — Nath, Goldberg & Meyer; Joshua B. Goldberg; Christopher Thomas

(57) ABSTRACT

Disclosed herein are a system and method for three-dimensional vibration measurement. The method includes measuring vibration components and shape information at a vibration measurement point of a measurement target by sequentially emitting laser beams to the vibration measurement point of the measurement target at each of three measuring positions for measuring vibration of the measurement target; obtaining transformation matrices between first to third coordinate systems with respect to each of the measuring positions and a local coordinate system with respect to the vibration measurement point of the measurement target, based on the shape information; measuring angles between unit vectors of respective axes of the local coordinate system and direction vectors of the laser beams emitted with reference to the first to third coordinate systems upon measuring the vibration components; and measuring three-dimensional vibration of the measurement target based on the vibration components and the angles.

15 Claims, 4 Drawing Sheets

(a)  (b)  (c)

US 9,310,341 B2

METHOD AND SYSTEM FOR THREE-DIMENSIONAL VIBRATION MEASUREMENT USING VIBROMETER

CROSS-REFERENCE TO RELATED APPLICATION

This application claims priority to Korean Patent Application No. 10-2012-0054093 filed on 22 May, 2012, and all the benefits accruing therefrom under 35 U.S.C. §119, the contents of which is incorporated by reference in its entirety.

BACKGROUND

1. Technical Field

Embodiments of the invention generally relate to vibration measurement, and more particularly, to a method and system for three-dimensional vibration measurement using a single vibrometer.

2. Description of the Related Art

A laser scanning vibrometer (LSV) is a device that employs an optical interferometer to measure a Doppler signal generated by vibration of a measurement target when a laser beam enters the measurement target, and employs a signal processor to convert the signal into a velocity signal, thereby measuring vibration. Due to characteristics of the device, a single laser scanning vibrometer can measure only one-dimensional (1D) vibration. Therefore, three laser scanning vibrometers are used to measure three-dimensional vibration.

A typical three-dimensional vibration measurement system includes three laser scanning vibrometers, a single laser range finder, and a frame for fixing relative locations between the laser scanning vibrometers and the laser range finder. Three-dimensional vibration measurement may be based on the relative locations of the three fixed laser scanning vibrometers, three-directional vibration components obtained from the laser scanning vibrometers, and shape information of a measurement target obtained from the laser range finder.

However, the typical three-dimensional vibration measurement system has a problem in that vibration measurement costs too much due to the use of at least three expensive laser scanning vibrometers. Thus, there is a need for a method and system for three-dimensional vibration measurement capable of considerably reducing costs for vibration measurement.

BRIEF SUMMARY

It is an aspect of the present invention to provide a method and system for three-dimensional vibration measurement, which can employ one vibrometer to measure three-dimensional vibration.

It is another aspect of the present invention to provide a method and system for three-dimensional vibration measurement, in which three-dimensional vibration can be measured in any direction without using a frame for fixing a vibrometer.

The present invention is not limited to the above aspects, and other aspects and technical problems (not mentioned above) of the invention will be clearly understood by those skilled in the art from the following description.

In accordance with one aspect of the present invention, a three-dimensional vibration measurement method includes: by a vibrometer and a distance-measuring device, measuring vibration components and shape information at a vibration measurement point of a measurement target by sequentially emitting laser beams to the vibration measurement point of the measurement target at each of three measuring positions for measuring vibration of the measurement target; by the distance-measuring device, obtaining transformation matrices between first to third coordinate systems with respect to each of the measuring positions and a local coordinate system with respect to the vibration measurement point of the measurement target, based on the shape information; by the vibrometer, measuring angles between unit vectors of respective axes of the local coordinate system and direction vectors of the laser beams emitted with reference to the first to third coordinate systems upon measuring the vibration components; and by the vibrometer, measuring three-dimensional vibration of the measurement target based on the vibration components and the angles.

The measuring vibration components and shape information may include: by the distance-measuring device, obtaining the shape information of the measurement target by measuring a distance from the measurement target; and measuring the vibration components at the vibration measurement point by sequentially emitting laser beams at each of the three measuring positions through a single vibrometer.

The obtaining transformation matrices includes: obtaining a transformation matrix between the first coordinate system and the local coordinate system with respect to the vibration measurement point of the measurement target, based on the shape information at the vibration measurement point obtained by the distance-measuring device; obtaining a transformation matrix between the first coordinate system and the second coordinate system with respect to the measuring position; and obtaining a transformation matrix between the first coordinate system and the third coordinate system with respect to the measuring position.

The measuring angles may include: transforming the unit vectors of the respective axes of the local coordinate system and the direction vectors of the first to third laser beams into the first coordinate system, using the transformation matrices between the first coordinate system (a coordinate system at the first measuring position among the three measuring positions), the local coordinate system at each vibration measurement point of the measurement target and the second to third coordinate systems; and measuring angles $\alpha$, $\beta$, $\gamma$ by applying an inner product between the unit vectors of the respective axes of the transformed local coordinated system and the transformed direction vectors of the first to third laser beams.

The measuring angles may include: by the vibrometer, measuring angles $\alpha_1$, $\beta_1$, $\gamma_1$ between a direction vector of a first laser beam emitted with reference to the first coordinate system and the unit vectors of the respective axes of the local coordinate system with reference to the first coordinate system transformed using a transformation matrix between the local coordinate system and the first coordinate system; by the vibrometer, measuring angles $\alpha_2$, $\beta_2$, $\gamma_2$ between the unit vectors of the respective axes of the local coordinate system with reference to the first coordinate system and direction vectors of a second laser beam transformed using a transformation matrix between the second coordinate system and the first coordinate system; and by the vibrometer, measuring angles $\alpha_3$, $\beta_3$, $\gamma_3$ between the unit vectors of the respective axes of the local coordinate system with reference to the first coordinate system and direction vectors of a third laser beam transformed using a transformation matrix between the third coordinate system and the first coordinate system.

The measuring three-dimensional vibration may include: measuring vibration components in a direction perpendicular to a measuring plane and vibration components in a direction parallel to the measuring plane at the vibration measurement point of the measurement target, using cosine values $\cos\alpha$, $\cos\beta$, $\cos\gamma$ of the angles $\alpha$, $\beta$, $\gamma$ and vibration components $V_1$, $V_2$, $V_3$ measured at the vibration measurement point according to three measuring positions.

The three measuring positions may be disposed in a triangular arrangement.

The three-dimensional vibration of the measurement target may be measured using a single vibrometer and a single distance-measuring device to measure vibration components and shape information a total of three times while changing the measuring positions.

The distance-measuring device may include a laser range finder, and the vibrometer may include a laser scanning vibrometer including a laser beam scanner disposed in a laser Doppler vibrometer.

In accordance with another aspect of the present invention, a system for measuring three-dimensional vibration of a measurement target using a single distance-measuring device and a single vibrometer is provided. In the system, the distance-measuring device obtains shape information regarding a vibration measurement point of a measurement target. The vibrometer measures vibration components at the vibration measurement point by sequentially emitting laser beams to the vibration measurement points of the measurement target according to three measuring positions, obtains transformation matrices between first to third coordinate systems with respect to each of the measuring positions and a local coordinate system with respect to the vibration measurement point of the measurement target, based on the shape information obtained by the distance-measuring device, measures angles between unit vectors of respective axes of the local coordinate system with reference to the local coordinate system upon measuring the vibration components and direction vectors of the laser beams emitted with reference to the first to third coordinates, and measures three-dimensional vibration of the measurement target based on the vibration components and the angles.

The distance-measuring device may measure a distance from the measurement target and obtain the shape information of the measurement target.

The vibrometer may measure vibration components at the vibration measurement point by sequentially emitting the laser beams at each of the three measuring positions.

The vibrometer may obtain a transformation matrix between the local coordinate system and the first coordinate system at the vibration measurement point of the measurement target, a transformation matrix between the local coordinate system and the second coordinate system at the vibration measurement point, and a transformation matrix between the local coordinate system and the third coordinate system at the vibration measurement point, based on the shape information at the vibration measurement point obtained by the distance-measuring device.

The vibrometer may transform the unit vectors of the respective axes of the local coordinate system and the direction vectors of the first to third laser beams into the first coordinate system, using the transformation matrices between the first coordinate system (a coordinate system at the first measuring position among the three measuring positions) and the local coordinate system at each vibration measurement point of the measurement target and the second to third coordinate systems; and measures angles $\alpha$, $\beta$, $\gamma$ by applying an inner product between the unit vectors of the respective axes of the transformed local coordinate system and the transformed direction vectors of the first to third laser beams.

The vibrometer measures angles $\alpha_1$, $\beta_1$, $\gamma_1$ between direction vectors of the first laser beam emitted with reference to the first coordinate system and the unit vectors of the respective axes of the local coordinate system with reference to the first coordinate system transformed using a transformation matrix between the local coordinate system and the first coordinate system, angles $\alpha_2$, $\beta_2$, $\gamma_2$ between the unit vectors of the respective axes of the local coordinate system with reference to the first coordinate system and direction vectors of the second laser beam transformed using a transformation matrix between the second coordinate system and the first coordinate system, and angles $\alpha_3$, $\beta_3$, $\gamma_3$ between the unit vectors of the respective axes of the local coordinate system with reference to the first coordinate system and direction vectors of the third laser beam transformed using a transformation matrix between the third coordinate system and the first coordinate system.

The vibrometer may measure vibration components in a direction perpendicular to a measuring plane and vibration components in a direction parallel to the measuring plane at the vibration measurement point of the measurement target, using cosine values $\cos \alpha$, $\cos \beta$, $\cos \gamma$ of the angles $\alpha$, $\beta$, $\gamma$ and vibration components $V_1$, $V_2$, $V_3$ measured at the vibration measurement point according to three measuring positions.

According to one embodiment, a single vibrometer is employed to measure three-dimensional vibration, thereby drastically reducing costs for vibration measurement.

According to one embodiment, three-dimensional vibration can be measured in any direction without using a frame for securing the vibrometer.

BRIEF DESCRIPTION OF THE DRAWINGS

The above and other aspects, features and advantages of the invention will become apparent from the following description of exemplary embodiments given in conjunction with the accompanying drawings, in which.

DETAILED DESCRIPTION

Figure 1:
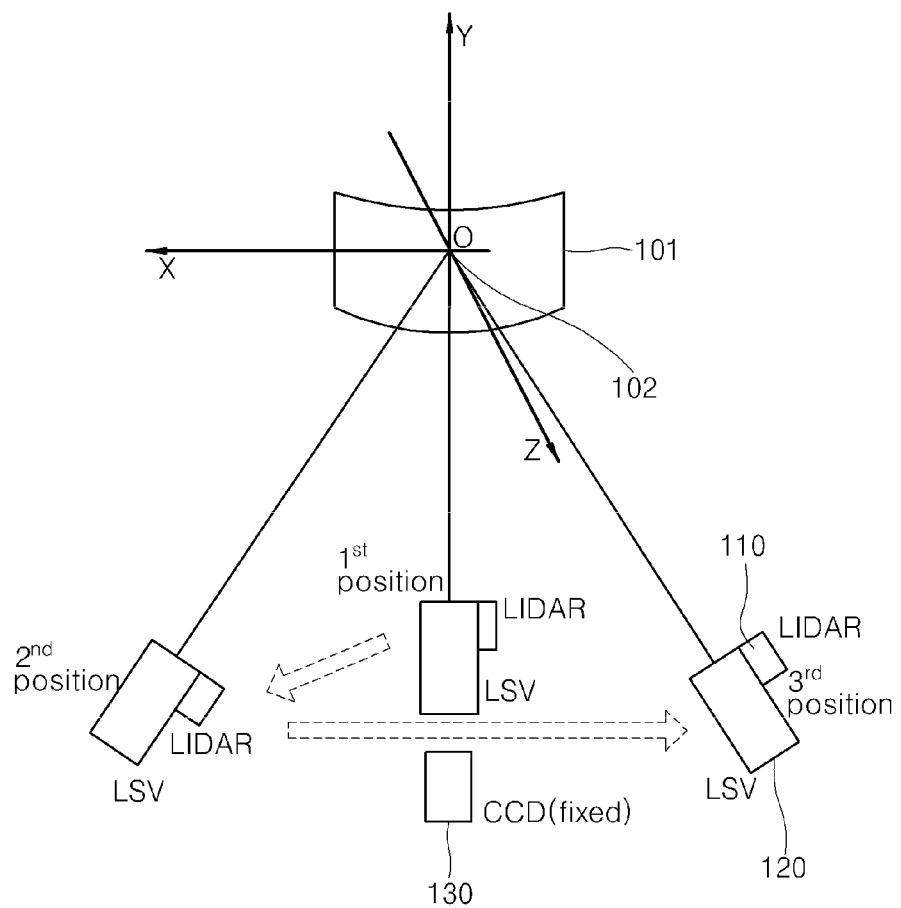
FIG. 1 is a conceptual view of a method and system for three-dimensional vibration measurement according to one embodiment of the present invention.

Hereinafter, embodiments of the invention will be described with reference to accompanying drawings. It should be understood that the present invention is not limited to the following embodiments and may be embodied in different ways, and that the embodiments are provided for complete disclosure and thorough understanding of the present invention by those skilled in the art. The scope of the invention is defined only by the claims and equivalents thereof. The same components will be denoted by the same reference numerals throughout the specification and the drawings.

A laser Doppler vibrometer (LDV) is a device that employs an optical interferometer to measure a Doppler signal generated by vibration of a measurement target when laser beams enter the measurement target, and employs a signal processor to convert the signal into a velocity signal, thereby performing contactless measurement of vibration.

To automatically measure many vibration measurement points, the laser Doppler vibrometer may be provided therein with a laser scanning vibrometer (LSV), which includes a laser beam scanner.

The laser scanning vibrometer makes it possible to safely and quickly perform experimental measurement as to vibration frequencies, vibration modes and operation modes (operational deflection shape, ODS) of an industrial structure or the like for engineering, architecture, mechanics, aeronautics and an electric system. Thus, the laser scanning vibrometer can be used to estimate various causes of vibration, noise, defects, and destruction due to vibration.

The laser scanning vibrometer performs contactless measurement. Such a laser scanning vibrometer can overcome disadvantages of load influence, impossibility of measuring a rotating body, and long measuring time, which are disadvantages of a contact vibrometer such as an existing accelerometer. For this reason, the laser scanning vibrometer can be used to measure rotating bodies and lightweight structures, and to perform long-range object measurement.

However, a single laser scanning vibrometer can measure vibration only in a traveling direction of the laser beam. Accordingly, if a single laser scanning vibrometer is used to measure vibration, it is possible to measure vibration generated in a direction perpendicular to a measuring plane at a vibration measurement point of the measurement target. On the other hand, it is impossible to measure vibration generated in a direction parallel with the measuring plane, and thus 3D-vibration measurement of the measurement target is also impossible.

To compensate for this, three laser scanning vibrometers (LSV) and a single laser range finder (light wave detection and ranging, LIDAR) secured by a frame have been used. Three laser scanning vibrometers can obtain velocity components of three directions (vibration components) based on shape information of the measurement target, obtained from the laser range finder at different three measuring positions, and thus three-dimensional vibration measurement of a measurement target is possible.

However, the foregoing method has a disadvantage that measurement is expensive because as many as three laser scanning vibrometers are needed. Frequency characteristics for analyzing the vibration measurement of an object are not related to time. Therefore, if only a single laser scanning vibrometer is used to measure vibration at one point (vibration measurement point) by changing measuring positions, the same effects as obtained by measuring vibration in three directions using three laser scanning vibrometers are achieved.

Accordingly, embodiments of the invention disclose a method and system for three-dimensional vibration measurement, in which a single vibrometer is employed to measure three-dimensional vibration, thereby drastically reducing costs for vibration measurement.

Embodiments of the invention will now be described in detail with reference to the accompanying drawings.

FIG. 1 is a conceptual view of a method and system for three-dimensional vibration measurement according to one embodiment of the present invention.

Referring to FIG. 1, a single laser range finder 110 and a single laser scanning vibrometer 120 may constitute an integrated system. The integrated system may employ a charge coupled device (CCD) 130 as an imaging device to precisely scan a vibration measurement point 102 of a measurement target 101 before measuring three-dimensional vibration of the measurement target 101 through the laser range finder 110 and the laser scanning vibrometer 120.

After complete scanning of the vibration measurement point 102 of the measurement target 101, the integrated system may obtain and measure shape information and vibration components of the vibration measurement point 102 of the measurement target 101 at each of three measuring positions ($1^{st}$ position, $2^{nd}$ position, and $3^{rd}$ position), while sequentially moving to the three measuring positions.

As a result, the integrated system may measure three-dimensional vibration of the measurement target 101. Here, the shape information may be obtained by the laser range finder 110, and the vibration components may be measured by the laser scanning vibrometer 120.

In this way, the integrated system employs a single laser range finder 110 and a single laser scanning vibrometer 120 to measure and obtain vibration components and shape information a total of three times while changing measuring positions, thereby measuring three-dimensional vibration of the measurement target 101. For reference, the integrated system will be described in more detail with reference to FIG. 3.

Figure 2:
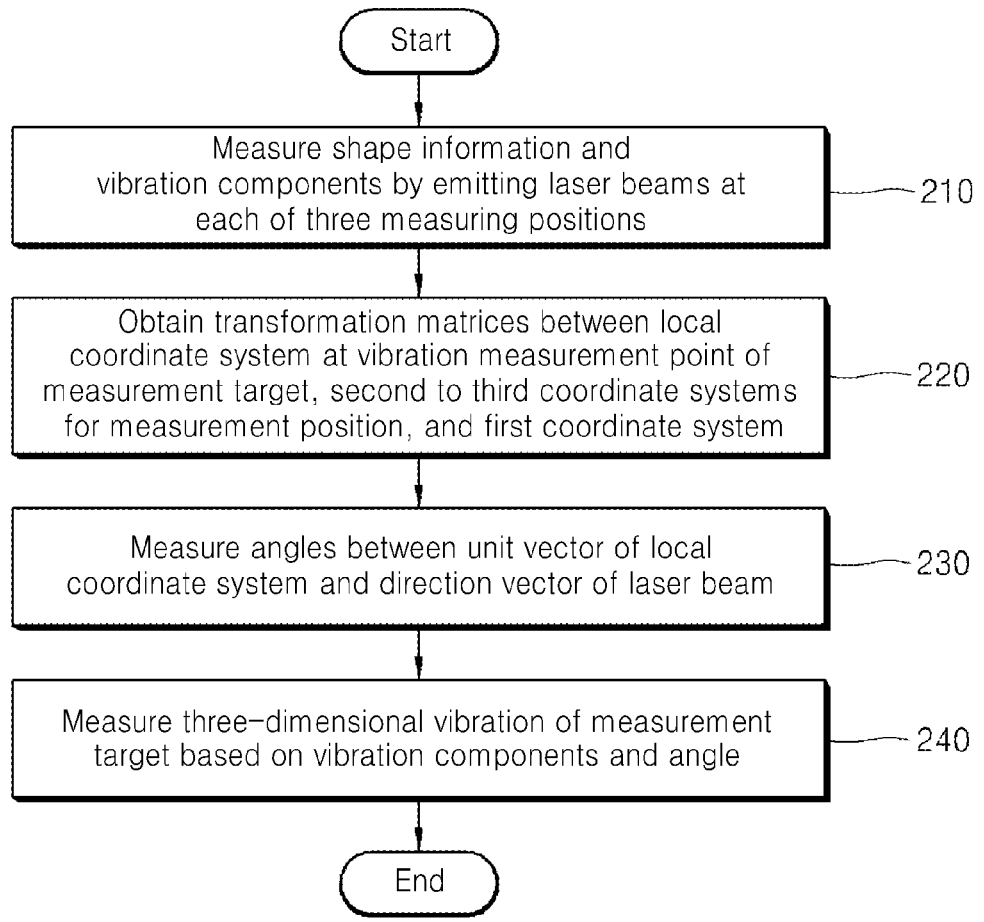
FIG. 2 is a flowchart of a three-dimensional vibration measurement method according to one embodiment of the present invention.

FIG. 2 is a flowchart of a three-dimensional vibration measurement method according to one embodiment of the present invention.

Referring to FIGS. 1 and 2, in operation 210, the laser range finder 110 and the laser scanning vibrometer 120 provide shape information and vibration components of the measurement target 101, respectively.

Specifically, the laser range finder 110 measures a distance from the measurement target 101 by emitting a laser beam to the measurement target 101 and obtains the shape information of the measurement target 101 based on the measured distance.

To this end, the laser range finder 110 can precisely scan the vibration measurement point 102 of the measurement target 101 through the CCD 130 and two scanning motors before obtaining the shape information, thereby preparing environments for obtaining the shape information.

In addition, the laser scanning vibrometer 120 sequentially emits laser beams to the vibration measurement point 102 of the measurement target 101 at each of three measuring positions, and measures vibration components at the vibration measurement point 102.

To this end, in one embodiment, a single laser scanning vibrometer 120 is used to measure the vibration components at the vibration measurement point 102 by sequentially emit laser beams to the vibration measurement point 102 at each of the three measuring positions. Here, the three measuring positions may constitute a triangular arrangement to enhance precision of three-dimensional vibration measurement with respect to the measurement target 101.

Next, in operation 220, based on the shape information at the vibration measurement point 102 of the measurement target 101 obtained by the laser range finder 110, transformation matrices between a first coordinate system $X_1Y_1Z_1$, a second coordinate system $X_2Y_2Z_2$, a third coordinate system $X_3Y_3Z_3$ with respect to the three measuring positions (the first, second and third positions) and a local coordinate system $X_LY_LZ_L$ with respect to the vibration measurement point 102 of the measurement target 101 are obtained to measure vibration of the measurement target 101.

Specifically, the shape information obtained by the laser range finder 110 includes information about the first to third coordinate systems with respect to the three measuring positions, respectively. Further, a normal vector at the vibration measurement point 102 is obtained, thereby obtaining information about the local coordinate system. Thus, when relationships between the local coordinate system and the first to third coordinate systems can be used, it is possible to obtain the transformation matrices between the first to third coordinate systems coordinate system $X_1Y_1Z_1$, $X_2Y_2Z_2$, $X_3Y_3Z_3$ and the local coordinate system $X_LY_LZ_L$.

Next, in operation 230, upon measuring the vibration components, the laser scanning vibrometer 120 measures angles between unit vectors of respective axes of the local coordinate system with respect to the first coordinate system and direction vectors of each of first to third laser beams emitted with reference to the first to third coordinate systems.

To this end, the laser scanning vibrometer 120 may measure angles $\alpha_1$, $\beta_1$, $\gamma_1$ between unit vectors of respective axes of the local coordinate system with respect to the first coordinate system, which is transformed by a transformation matrix between the local coordinate system and the first coordinate system, and the direction vectors of the first laser beam emitted with reference to the first coordinate system.

In addition, the laser scanning vibrometer 120 may measure angles $\alpha_2$, $\beta_2$, $\gamma_2$ between the unit vectors of the respective axes of the local coordinate system with respect to the first coordinate system and direction vectors of the second laser beam, which is transformed by a transformation matrix between the second coordinate system and the first coordinate system.

Further, the laser scanning vibrometer 120 may measure angles $\alpha_3$, $\beta_3$, $\gamma_3$ between the unit vectors of the respective axes of the local coordinate system with respect to the first coordinate system and direction vectors of the third laser beam, which is transformed by a transformation matrix between the second coordinate system and the first coordinate system.

Specifically, the laser scanning vibrometer 120 may transform the unit vectors of the respective axes of the local coordinate system into the first coordinate system through the transformation matrix derived between the first coordinate system (i.e., the coordinate system at the first measuring position) and the local coordinate system at the vibration measurement point 102 of the measurement target 101. Additionally, the laser scanning vibrometer 120 may transform the direction vectors of the first to third laser beams into the first coordinate system through the transformation matrix derived between the first coordinate system (i.e., the coordinate system at the first measuring position among the three measuring positions) and the second and third coordinate systems (i.e., the coordinate systems at the second and third measuring positions). Further, the laser scanning vibrometer 120 may measure the angles $\alpha$, $\beta$, $\gamma$ by applying an inner product between the unit vectors of the respective axes of the transformed local coordinate system and the transformed first to third direction vectors.

Next, in operation 240, the laser scanning vibrometer 120 uses the vibration components and the angles to measure three-dimensional vibration of the measurement target 101.

That is, the laser scanning vibrometer 120 uses cosine values $\cos\alpha$, $\cos\beta$, $\cos\gamma$ of the angles $\alpha$, $\beta$, $\gamma$ and the vibration components $V_1$, $V_2$, $V_3$ at the vibration measurement point 102 according to three measuring positions, thereby measuring a vibration component in a direction perpendicular to the measuring plane and a vibration component in a direction parallel to the measuring plane at the vibration measurement point 102 of the measurement target 101, i.e., measuring three-dimensional vibration.

Figure 3:
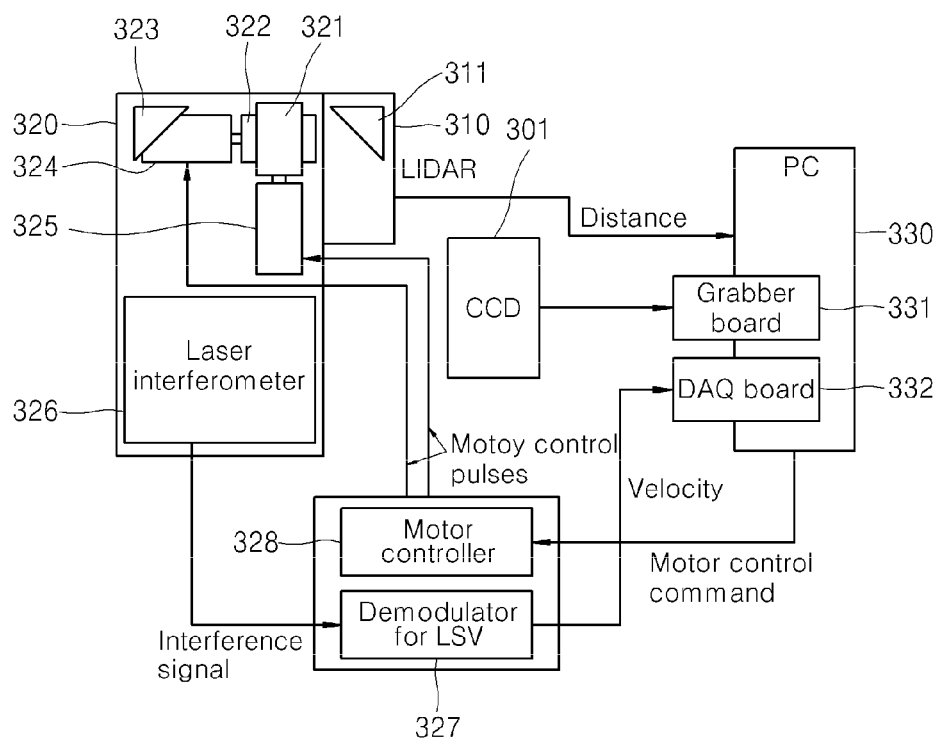
FIG. 3 is a block diagram of a three-dimensional vibration measurement system according to one embodiment of the present invention.

FIG. 3 is a block diagram of a three-dimensional vibration measurement system according to one embodiment of the present invention.

Referring to FIG. 3, according to the present embodiment, a three-dimensional vibration measurement system 300 may include a single laser range finder 310 and a single laser scanning vibrometer 320. Here, the laser range finder 310 and the laser scanning vibrometer 320 may constitute an integrated system.

Further, the three-dimensional vibration measurement system 300 may further include a CCD 301 for capturing an image of a measurement target; motors 324, 325 for precisely scanning a vibration measurement point of the measurement target together with the CCD 301; a motor controller 328 for controlling operation of the motors 324, 325; stationary mirrors 311, 323; mirrors 321, 322 adjusted to have a predetermined angle by operation of the motors 324, 325; a laser interferometer 326 for receiving a laser beam reflected by the measurement target and outputting an interference signal; a demodulator 327 for processing the interference signal and outputting vibration components (velocity), a Grabber board 331 for receiving video information from the CCD 301, and a personal computer (PC) 330 including a DAQ board 332 for receiving the measured distance value and the vibration components from the laser range finder 110 and the demodulator 327, respectively.

Here, the demodulator 327 and the motor controller 328 may be disposed inside the laser scanning vibrometer 120, or may be separately provided. Further, the PC 330 may be disposed within the laser range finder 120 and the laser scanning vibrometer 120.

Figure 4:
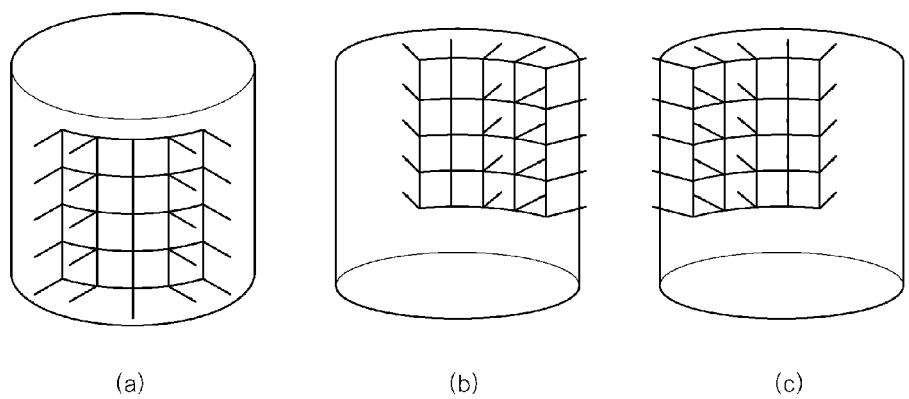
FIG. 4 is a view showing shape information and normal vectors of a measurement target measured at different measuring points according to one embodiment of the present invention.
Figure 5:
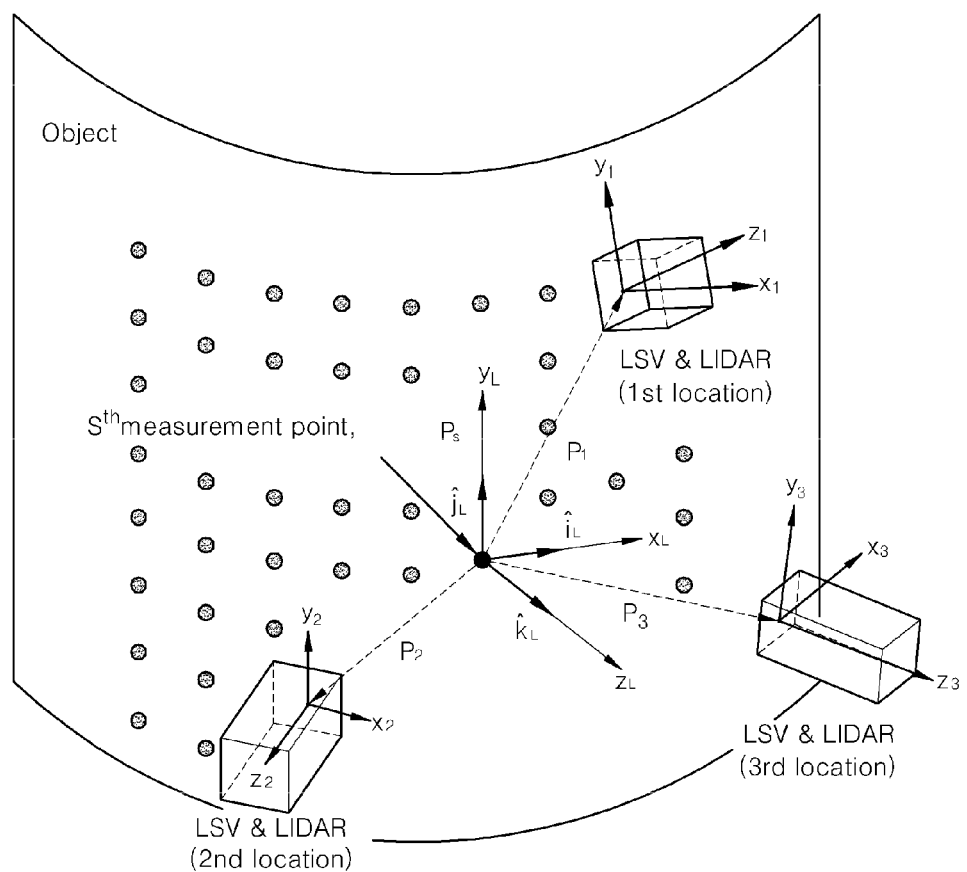
FIG. 5 is a three-dimensional view showing an example of the three-dimensional vibration measurement method employing a single laser scanning vibrometer.

According to one embodiment of the invention, the three-dimensional vibration measurement system operates as follows. For reference, FIG. 4 is a view showing shape information and normal vectors of the measurement target measured at different measuring points according to one embodiment of the present invention, and FIG. 5 is a three-dimensional view showing an example of the three-dimensional vibration measurement method using a single laser scanning vibrometer.

First, the laser range finder 110 may obtain a normal vector at a vibration measurement point of the measurement target at each measuring position (i.e. each of three measuring positions). Since the normal vectors obtained at the respective measuring positions are obtained with respect to the same vibration measurement point at the different measuring positions, the normal vectors at the vibration measurement point are oriented in different directions from one another, as shown in FIG. 4.

However, the relationship between the normal vectors of the shape information obtained at one measuring position is the same as that obtained at another measuring position. Therefore, if shape information obtained at a certain measuring position is rotated by a proper angle, it may exactly correspond to shape information obtained at another measuring position. This relationship may be represented by the following Expressions 1 and 2.

$$(n)_{x_1y_1z_1} = R_{12} \times (n)_{x_2y_2z_2} + e_{12} \quad \text{[Expression 1]}$$

$$(n)_{x_1y_1z_1} = R_{13} \times (n)_{x_3y_3z_3} + e_{13} \quad \text{[Expression 2]}$$

In the above Expressions 1 and 2, $(n)_{x_1y_1z_1}$, $(n)_{x_2y_2z_2}$, and $(n)_{x_3y_3z_3}$ are normal vectors at a certain vibration measurement point obtained at each measuring position; and $R_{12}$ and $R_{13}$ are transformation matrixes between the coordinate system $x_1y_1z_1$ at the first measuring position and the coordinate systems $x_2y_2z_2$ and $x_2y_3z_3$ at the second and third measuring positions. Additionally, $e_{12}$ and $e_{13}$ means errors generated in the course of vibration measurement.

Expressions 1 and 2 may be represented with respect to the errors by the following Expressions 3 and 4.

$$e_{12} = (n)_{x_1y_1z_1} - R_{12} \times (n)_{x_2y_2z_2}$$ [Expression 3]

$$e_{13} = (n)_{x_1y_1z_1} - R_{13} \times (n)_{x_3y_3z_3}$$ [Expression 4]

Here, an error generated at each vibration measurement point is obtained in the form of a vector value and the magnitude thereof represents the sum of squares of error components. By summing all of the errors generated at the vibration measurement points, the sum $\epsilon_{lsm}$ of the errors generated at all the vibration measurement points may be represented by the following Expressions 5 and 6.

$$\epsilon_{lsm,12} = \sum_{i=1}^{n} (|e_{i,12}|^2)$$ [Expression 5]

$$= \sum_{i=1}^{n} \left( \left| (n_i)_{x_1y_1z_1} - R_{12} \times (n_i)_{x_2y_2z_2} \right|^2 \right)$$

$$\epsilon_{lsm,13} = \sum_{i=1}^{n} (|e_{i,13}|^2)$$ [Expression 6]

$$= \sum_{i=1}^{n} \left( \left| (n_i)_{x_1y_1z_1} - R_{13} \times (n_i)_{x_3y_3z_3} \right|^2 \right)$$

In Expressions 5 and 6, i refers to a measuring order for many vibration measurement points at a certain measuring position, and means that the transformation matrix more precisely represents the relationship between two coordinate systems, as becomes $\epsilon_{lsm}$ smaller. $\epsilon_{lsm}$ is obtained by applying every possible transformation matrix to Expressions 5 and 6, and the transformation matrix at the smallest $\epsilon_{lsm}$ may be used as the transformation matrices $R_{12}$ and $R_{13}$ between two coordinate systems. In this way, it is possible to obtain the transformation matrix $R_{1L}$ between the coordinate system $x_1y_1z_1$ at the first measuring position and the local coordinate system $x_Ly_Lz_L$ at each vibration measurement point.

The transformation matrices obtained as above may be used to obtain the angles α, β, γ between the local coordinate axes and a laser beam in the following Expression 12. As shown in FIG. 5, let the unit vectors of the local coordinate axes xL, yL, zL be $\hat{i}_L$, $\hat{j}_L$, $\hat{k}_L$, and let the vectors of the laser beam toward the origin of the coordinate systems $x_1y_1z_1$, $x_2y_2z_2$, $x_3y_3z_3$ in each measuring position at the vibration measurement point be P1, P2, P3. Here, unit vectors $(\hat{i}_L)_{x_Ly_Lz_L}$, $(\hat{j}_L)_{x_Ly_Lz_L}$, $(\hat{k}_L)_{x_Ly_Lz_L}$, obtained with respect to the local coordinate system $x_Ly_Lz_L$ and vectors $(P_1)_{x_1y_1z_1}$, $(P_2)_{x_2y_2z_2}$, $(P_3)_{x_3y_3z_3}$ of the laser beam obtained with respect to the coordinate system at each measuring point (i.e., the first to third coordinate systems) are all transformed into the coordinate systems $x_1y_1z_1$ at the first measuring position, i.e., the first coordinate system, as shown in the following Expressions 7 and 8, based on the transformation matrices $R_{12}$, $R_{13}$, $R_{1L}$ obtained as above.

$$(P_2)_{x_1y_1z_1} = R_{12} \times (P_2)_{x_2y_2z_2}, (P_3)_{x_1y_1z_1} = R_{13} \times (P_3)_{x_3y_3z_3}$$ [Expression 7]

$$(\hat{i}_L)_{x_1y_1z_1} = R_{1L} \times (\hat{i}_L)_{x_Ly_Lz_L}, (\hat{j}_L)_{x_1y_1z_1} = R_{1L} \times (\hat{j}_L)_{x_Ly_Lz_L},$$
$$(\hat{k}_L)_{x_1y_1z_1} = R_{1L} \times (\hat{k}_L)_{x_Ly_Lz_L}$$ [Expression 8]

Finally, the angles between the unit vector of the local coordinate axes and the vectors of the laser beam can be obtained from the inner product between the vectors transformed, as shown in the following Expressions 9, 10 and 11.

$$\cos\alpha_k = \frac{(\hat{i}_L)_{x_1y_1z_1} \cdot (P_k)_{x_1y_1z_1}}{|(\hat{i}_L)_{x_1y_1z_1}||(P_k)_{x_1y_1z_1}|}$$ [Expression 9]

$$\cos\beta_k = \frac{(\hat{j}_L)_{x_1y_1z_1} \cdot (P_k)_{x_1y_1z_1}}{|(\hat{j}_L)_{x_1y_1z_1}||(P_k)_{x_1y_1z_1}|}$$ [Expression 10]

$$\cos\gamma_k = \frac{(\hat{k}_L)_{x_1y_1z_1} \cdot (P_k)_{x_1y_1z_1}}{|(\hat{k}_L)_{x_1y_1z_1}||(P_k)_{x_1y_1z_1}|}$$ [Expression 11]

In Expressions 9, 10 and 11, subscript k indicates the order of the measuring position. This applies to all of vibration measurement points. Such obtained cosine values at all of the vibration measurement points and vibration components $V_1$, $V_2$, $V_3$ measured by the laser scanning vibrometer 120 at the respective measuring positions are applied to the following Expression 12, so that vibration $V_z$ in a direction perpendicular to the measuring plane and vibration $V_x$ and $V_y$ in a direction parallel to the measuring plane can be obtained at each vibration measurement point.

$$\begin{pmatrix} V_x \\ V_y \\ V_z \end{pmatrix} = \begin{pmatrix} \cos\alpha_1 & \cos\beta_1 & \cos\gamma_1 \\ \cos\alpha_2 & \cos\beta_2 & \cos\gamma_2 \\ \cos\alpha_3 & \cos\beta_3 & \cos\gamma_3 \end{pmatrix}^{-1} \begin{pmatrix} V_1 \\ V_2 \\ V_3 \end{pmatrix}$$ [Expression 12]

In this way, according to one embodiment of the invention, a single laser scanning vibrometer and a single laser range finder are used to measure three-dimensional vibration, whereby costs for vibration measurement costs can be drastically reduced. Additionally, according to the one embodiment, three-dimensional vibration can be measured in any direction at properly triangulated positions without using a frame for securing the laser scanning vibrometer.

The embodiments of the present invention may be realized in the form of program instructions which can be implemented through various computer components, and may be recorded in a computer-readable storage medium. The computer-readable storage medium may include a program instruction, a local data file, a local data structure, and the like either alone or in combination thereof. The program instruction recorded in the computer-readable storage medium may be any program instruction particularly designed and structured for the present invention or known to those skilled in the field of computer software. Examples of the computer-readable storage medium include magnetic recording media such as hard disks, floppy disks and magnetic tapes, optical data storage media such as CD-ROMs or DVD-ROMs, magneto-optical media such as floptical disks, and hardware devices, such as read-only memory (ROM), random-access memory (RAM), and flash memory, which are particularly structured to store and implement the program instruction. Examples of the program instruction include not only machine language code generated by a compiler but also high level language code which can be executed by a computer using an interpreter.

Although some embodiments have been described herein, it should be understood by those skilled in the art that these embodiments are given by way of illustration only, and that various modifications, variations, and alterations can be made without departing from the spirit and scope of the present invention. Accordingly, the scope of the present invention should be limited only by the accompanying claims and equivalents thereof.

What is claimed is:

1. A three-dimensional vibration measurement method comprising:
by a distance-measuring device, obtaining shape information of a measurement target by measuring a distance from the measurement target;
by a vibrometer, sequentially emitting laser beams to a vibration measurement point of the measurement target at each of three measuring positions for measuring vibration of the measurement target to measure vibration components at the vibration measurement point;
by the vibrometer, obtaining transformation matrices between first to third coordinate systems with respect to each of the measuring positions and a local coordinate system with respect to the vibration measurement point of the measurement target, based on the shape information obtained by the distance-measuring device;
by the vibrometer, measuring angles between unit vectors of respective axes of the local coordinate system and direction vectors of the laser beams emitted with reference to the first to third coordinate systems upon measuring the vibration components; and
by the vibrometer, measuring three-dimensional vibration of the measurement target based on the vibration components and the angles.

2. The three-dimensional vibration measurement method according to claim 1, wherein the obtaining the transformation matrix comprises:
obtaining a transformation matrix between the first coordinate system and the local coordinate system with respect to the vibration measurement point of the measurement target, based on the shape information obtained by the distance-measuring device;
obtaining a transformation matrix between the first coordinate system and the second coordinate system with respect to the measuring position, based on the shape information obtained by the distance-measuring device; and
obtaining a transformation matrix between the first coordinate system and the third coordinate system with respect to the measuring position, based on the shape information obtained by the distance-measuring device.

3. The three-dimensional vibration measurement method according to claim 1, wherein the measuring angles comprises:
transforming the unit vectors of the respective axes of the local coordinate system and the direction vectors of first to third laser beams into the first coordinate system, using the transformation matrices between the first coordinate system (a coordinate system at the first measuring position among the three measuring positions), the local coordinate system at each vibration measurement point of the measurement target and the second to third coordinate systems; and
measuring angles $\alpha$, $\beta$, $\gamma$ by applying an inner product between the unit vectors of the respective axes of the transformed local coordinated system and the transformed direction vectors of the first to third laser beams.

4. The three-dimensional vibration measurement method according to claim 1, wherein the measuring angles comprises:
measuring angles $\alpha_1$, $\beta_1$, $\gamma_1$ between direction vectors of a first laser beam emitted with reference to the first coordinate system and the unit vectors of the respective axes of the local coordinate system with reference to the first coordinate system transformed using a transformation matrix between the local coordinate system and the first coordinate system;
measuring angles $\alpha_2$, $\beta_2$, $\gamma_2$ between the unit vectors of the respective axes of the local coordinate system with reference to the first coordinate system and direction vectors of a second laser beam transformed using a transformation matrix between the second coordinate system and the first coordinate system; and
measuring angles $\alpha_3$, $\beta_3$, $\gamma_3$ between the unit vectors of the respective axes of the local coordinate system with reference to the first coordinate system and direction vectors of a third laser beam transformed using a transformation matrix between the third coordinate system and the first coordinate system.

5. The three-dimensional vibration measurement method according to claim 1, wherein the measuring three-dimensional vibration comprises:
measuring vibration components in a direction perpendicular to a measuring plane and vibration components in a direction parallel to the measuring plane at the vibration measurement point of the measurement target, using cosine values $\cos\alpha$, $\cos\beta$, $\cos\gamma$ of the angles $\alpha$, $\beta$, $\gamma$ and vibration components $V_1$, $V_2$, $V_3$ measured at the vibration measurement point according to the three measuring positions.

6. The three-dimensional vibration measurement method according to claim 1, wherein the three measuring positions are disposed in a triangular arrangement.

7. The three-dimensional vibration measurement method according to claim 1, wherein the three-dimensional vibration of the measurement target is measured using a single vibrometer and a single distance-measuring device to measure vibration components and shape information a total of three times while changing the measuring positions.

8. The three-dimensional vibration measurement method according to claim 1, wherein the distance-measuring device comprises a laser range finder, and the vibrometer comprises a laser scanning vibrometer including a laser beam scanner disposed in a laser Doppler vibrometer.

9. A system for measuring three-dimensional vibration of a measurement target using a single distance-measuring device and a single vibrometer,
wherein the distance-measuring device obtains shape information regarding a vibration measurement point of a measurement target; and
wherein the vibrometer which measures vibration components at the vibration measurement point by sequentially emitting laser beams to the vibration measurement point of the measurement target at each of three measuring positions, obtains transformation matrices between first to third coordinate systems with respect to each of the measuring positions and a local coordinate system with respect to the vibration measurement point of the measurement target, based on the shape information obtained by the distance-measuring device, measures angles between unit vectors of respective axes of the local coordinate system with reference to the local coordinate system upon measuring the vibration components and direction vectors of the laser beams emitted with reference to the first to third coordinates, and measures three-dimensional vibration of the measurement target based on the vibration components and the angles.

10. The system according to claim 9, wherein the distance-measuring device measures a distance from the measurement target and obtains the shape information of the measurement target.

11. The system according to claim 9, wherein the vibrometer measures the vibration components at the vibration measurement point by sequentially emitting the laser beams at each of the three measuring positions.

12. The system according to claim 9, wherein the vibrometer obtains a transformation matrix between the first coordinate system and the local coordinate system with respect to the vibration measurement point of the measurement target, a transformation matrix between the first coordinate system and the second coordinate system with respect to the measuring position, and a transformation matrix between the first coordinate system and the third coordinate system with respect to the measuring position, based on the shape information at the vibration measurement point obtained by the distance-measuring device.

13. The system according to claim 9, wherein the vibrometer transforms the unit vectors of the respective axes of the local coordinate system and direction vectors of first to third laser beams into the first coordinate system, using the transformation matrices between the first coordinate system (a coordinate system at the first measuring position among the three measuring positions), the local coordinate system at each vibration measurement point of the measurement target and the second to third coordinate systems, and measures angles $\alpha$, $\beta$, $\gamma$ by applying an inner product between the unit vectors of the respective axes of the transformed local coordinated system and the transformed direction vectors of the first to third laser beams.

14. The system according to claim 13, wherein the vibrometer measures angles $\alpha_1$, $\beta_1$, $\gamma_1$ between the direction vectors of the first laser beam emitted with reference to the first coordinate system and the unit vectors of the respective axes of the local coordinate system with reference to the first coordinate system transformed using a transformation matrix between the local coordinate system and the first coordinate system, measures angles $\alpha_2$, $\beta_2$, $\gamma_2$ between the unit vectors of the respective axes of the local coordinate system with reference to the first coordinate system and the direction vectors of the second laser beam transformed using a transformation matrix between the second coordinate system and the first coordinate system, and measures angles $\alpha_3$, $\beta_3$, $\gamma_3$ between the unit vectors of the respective axes of the local coordinate system with reference to the first coordinate system and the direction vectors of the third laser beam transformed using a transformation matrix between the third coordinate system and the first coordinate system.

15. The system according to claim 9, wherein the vibrometer measures vibration components in a direction perpendicular to a measuring plane and vibration components in a direction parallel to the measuring plane at the vibration measurement point of the measurement target, using cosine values $\cos\alpha$, $\cos\beta$, $\cos\gamma$ of the angles $\alpha$, $\beta$, $\gamma$ and vibration components $V_1$, $V_2$, $V_3$ measured at the vibration measurement point according to the three measuring positions.

* * * * *